(12) United States Patent
Solarz

(10) Patent No.: US 8,218,221 B1
(45) Date of Patent: Jul. 10, 2012

(54) INDIUM RICH INGAN LED LINE MONITOR

(75) Inventor: Richard W. Solarz, Danville, CA (US)

(73) Assignee: KLA-Tencor Corporation, Milpitas, CA (US)

(*) Notice: Subject to any disclaimer, the term of this patent is extended or adjusted under 35 U.S.C. 154(b) by 994 days.

(21) Appl. No.: 12/195,271

(22) Filed: Aug. 20, 2008

Related U.S. Application Data

(60) Provisional application No. 60/957,080, filed on Aug. 21, 2007.

(51) Int. Cl.
*G02F 1/03* (2006.01)
*G02F 1/01* (2006.01)
*H01L 29/06* (2006.01)
*H01S 5/00* (2006.01)

(52) U.S. Cl. ...... 359/244; 359/240; 257/14; 372/45.012

(58) Field of Classification Search .................. 359/244, 359/240, 245, 248, 250–252, 255–256, 315, 359/321; 385/14, 122, 129–131, 2; 372/45.01, 372/45.011, 7, 11, 18, 43, 45, 48, 68, 75; 257/18, 14–15, 189, 622–623
See application file for complete search history.

(56) References Cited

U.S. PATENT DOCUMENTS

| | | | |
|---|---|---|---|
| 4,503,477 A | * | 3/1985 | Henriksen et al. ............. 361/2 |
| 6,541,788 B2 | * | 4/2003 | Petroff et al. ................. 257/21 |
| 2008/0088903 A1 | | 4/2008 | Matteo et al. |

OTHER PUBLICATIONS

Matteo et al. "Spectral analysis of strongly enhanced visible light transmission through single C-shaped nanoapertures," Applied Physics Letters, vol. 85, No. 4, Jul. 26, 2004, pp. 648-650.

Usov et al. "Analysis of the local indium composition in ultrathin InGaN layers," Semiconductor Science and Technology 22 (2007) 528-532.

Kim et al. "Characterisation of Optical Properties in Micro-Patterned InGaN Quantum Wells," Phys. Stat. Sol. (b) 228, No. 1, 169-172 (2001).

Qi et al. "Comparison of blue and green InGaN/GaN multiple-quantum-well light-emitting diodes grown by metalorganic vapor phase epitaxy," Applied Physics Letters 86, 101903 (2005).

Bessolov et al. "Dependence of GaN Photoluminescence on the Excitation Intensity," Semiconductors, vol. 36, No. 10, 2002, pp. 1128-1131.

Chang et al. "Direct evidence of nanocluster-induced luminescence in InGaN epifilms," Applied Physics Letters 86, 021911 (2005).

(Continued)

*Primary Examiner* — Dawayne A Pinkney
(74) *Attorney, Agent, or Firm* — Bever, Hoffman & Harms, LLP; Jeanette S. Harms

(57) ABSTRACT

A method of generating a photoluminescence map for an indium gallium nitride (InGaN) well can include presenting data on a pixel by pixel basis. The data can be generated as a function of emission wavelength, line width of emission, polarization of emission, and intensity of emission. The data can also be generated as a function of excitation polarization and polarization angle orientation with respect to film crystalline axes of the InGaN well. The data can also be generated as a function of multiple wavelengths of light to generate the photoluminescence map. The photoluminescence maps can be correlated to device internal quantum efficiency as measured in test devices. The resulting correlation maps can serve as line monitors of indium rich InGaN wafers used for green LEDs.

10 Claims, 2 Drawing Sheets

OTHER PUBLICATIONS

Cho et al. "Effect of growth interruptions on the light emission and indium clustering of InGaN/GaN multiple quantum wells," Applied Physics Letters, vol. 79, No. 16, Oct. 15, 2001, pp. 2594-2596.

Liu et al. "Effect of indium segregation on optical and structural properties of GaInNAs/GaAs quantum wells at emission wavelength of 1.3 μm," Journal of Applied Physics 100, 083518 (2006).

Soltani Vala et al. "Effects of Indium Segregation and Well-Width Fluctuations on Optical Properties of InGaN/GaN Quantum Wells," Phys. Stat. Sol. (b) 228, No. 2, pp. 453-456 (2001).

Moon et al. "Effects of thermal and hydrogen treatment on indium segregation in InGaN/GaN multiple quantum wells," Journal of Applied Physics, vol. 89, No. 11, Jun. 1, 2001, pp. 6514-6518.

EpiEL™ Mapping Technology promotional brochure, MaxMile Technologies, LLC, Sep. 2006.

Wetzel et al. "GaInN/GaN growth optimization for high-power green light-emitting diodes," Applied Physics Letters, vol. 85, No. 6, Aug. 9, 2004, pp. 866-868.

Kadir et al. "Growth and characterization of InN layers by metal-organic vapour phase epitaxy in a close-coupled showerhead reactor," Journal of Crystal Growth 298 (2007) pp. 403-408.

Komaki et al. "Growth of In-rich InGaN films on sapphire via GaN Layer by RF-MBE," Journal of Crystal Growth 301-302 (2007) pp. 473-477.

Wang et al. "In situ spectroscopic ellipsometry and RHEED monitored growth of InN nanocolumns by molecular beam epitaxy," Journal of Crystal Growth 301-302 (2007) pp. 496-499.

Micheletto et al. "Indium concentration influence on PL spatial inhomogeneity in InGaN single quantum well structures detected by original low-cost near-field probes," Applied Surface Science 229 (2004) pp. 338-345.

Duxbury et al. "Indium segregation in InGaN quantum-well structures," Applied Physics Letters, vol. 76, No. 12, Mar. 20, 2000, pp. 1600-1602.

Talalaev et al. "Indium Segregation in MOVPE Grown InGaN-Based Heterostructures," Phys. Stat. Sol. (c) 0, No. 1, pp. 311-314 (2002).

Gerthsen et al. "InGaN composition and growth rate during the early stages of metalorganic chemical vapor deposition," Applied Physics Letters, vol. 79, No. 16, Oct. 15, 2001, pp. 2552-2554.

Florescu et al. "Investigation of V-Defects and embedded inclusions in InGaN/GaN multiple quantum wells grown by metalorganic chemical vapor deposition on (0001) sapphire," Applied Physics Letters, vol. 83, No. 1, Jul. 7, 2003, pp. 33-35.

Nakamura, Shuji "Present performance of InGaN based blue/green/yellow LEDs," SPIE, vol. 3002, Apr. 1997, pp. 26-35.

Martin et al. "Light emission ranging from blue to red from a series of InGaN/GaN single quantum wells," J. Phys. D: Appl. Phys. 35 (2002) pp. 604-608.

Jinschek et al. "Local indium segregation and bang gap variations in high efficiency green light emitting InGaN/GaN diodes," Solid State Communications 137 (2006) pp. 230-234.

Bertram et al. "Microscopic correlation of redshifted luminescence and surface defects in thick $In_xGa_{1-x}N$ layers," Applied Physics Letters, vol. 80, No. 19, May 13, 2002, pp. 3524-3526.

Costa et al. "Misfit dislocations in In-rich InGaN/GaN quantum well structures," Phys. Stat. Sol. (a) 203, No. 7 (2006) pp. 1729-1732.

Talalaev et al. "On the Possible Origins of Low Indium Incorporation during MOVPE of InGaN," Phys. Stat. Sol. (a) 176 (1999) pp. 253-256.

Cheung et al. "Photoluminescence study of MBE grown InGaN with intentional indium segregation," Phys. Stat. Sol. (c) 2, No. 7 (2005) pp. 2779-2782.

Howe et al. "Quantification of segregation and strain effects in InAs/GaAs quantum dot growth," Journal of Applied Physics 98 (2005) 5 pages.

Jursenas et al. "Quantum-well thickness dependence of stimulated emission in InGaN/GaN structures," Phys. Stat. Sol. (c) 0, No. 7 (2003) pp. 2610-2613.

Nakamura et al. "RF-MBE growth and structural characterization of cubic InN films on yttria-stabilized zirconia (001) substrates," Journal of Crystal Growth 301-302 (2007) pp. 508-512.

Cho et al. "Structural and Optical Characteristics of InGaN/GaN Multiple Quantum Wells with Different Growth Interruption," Phys. Stat. Sol. (b) 228, No. 1 (2001) pp. 165-168.

Dimitrakopulos et al. "Structural properties of quaternary InAlGaN MQW grown by plasma-assisted MBE," Phys. Stat. Sol. (a) 203, No. 9, (2006) pp. 2151-2155.

Cao et al. "Temperature-Dependent Electroluminescence of AlGaN-Based UV LEDs," IEEE Electron Device Letters, vol. 27, No. 5, May 2006, pp. 329-331.

G. Gonzalez de la Cruz "The influence of surface segregation on the optical properties of quantum wells," Journal of Applied Physics, vol. 96, No. 7, Oct. 1, 2004, pp. 3752-3755.

\* cited by examiner

INDIUM RICH INGAN LED LINE MONITOR

RELATED APPLICATIONS

This application is a non-provisional of U.S. Patent Application 60/957,080, entitled "Heavily Indium Doped InGaN LED Film Line Monitor" filed Aug. 21, 2007.

BACKGROUND OF THE INVENTION

1. Field of the Invention

The present invention relates to LEDs and in particular to an improved line monitor for indium rich (green) InGaN LEDs.

2. Related Art

The rapidly emerging LED industry is poised to soon intersect the commercial and residential lighting market. As a result, growth in the LED industry is expected to accelerate dramatically. This emerging industry is also poised for the insertion of yield management technologies, just as silicon manufacturing was 30 years ago.

One of the most difficult problems in LED manufacturing is the growth of LEDs that emit light in the green region of the electromagnetic spectrum. In general, LEDs are manufactured from indium gallium nitride ($In_xGa_{(1-x)}N$)(wherein X varies as indicated below and is deleted for simplicity hereafter). Indium compositions of only a few percent are required for "blue" LEDs. However, indium content from ten to twenty percent is required for bandgaps that provide light in the green region of the electromagnetic spectrum. As used herein, this content percentage of indium is referenced as "indium rich" InGaN.

Unfortunately, it is well known that indium rich InGaN quantum wells do not grow with uniform film composition. Due to the difference in surface mobilities, strain between the indium rich InGaN quantum wells and its corresponding GaN confinement layers, and other physical considerations, the indium rich InGaN material generally exhibits "clustering" of the indium. Namely, the quantum well is no longer homogeneous in indium composition but instead exhibits a film of widely varying indium composition.

FIG. 1 illustrates an exemplary cross-section of an LED 100 having an InGaN well. In LED 100, a substrate 101 is typically formed from sapphire or silicon carbide. Substrates of AlN or bulk GaN are also being considered. Barrier layer 102 is formed on substrate 101. N-type layer 103 is formed on barrier layer 102. P-type layer 105 is formed on n-type layer 103. N-type layer 103 and p-type layer 105 can be made from gallium nitride (GaN) with n-type and p-type doping, respectively. A quantum well 104, which is formed between n-type layer 103 and p-type layer 105, is actually a very thin well on the order of 10-20 nanometers thick, but is shown thicker for illustration purposes (i.e. compared to n-type layer 103 and p-type layer 105, which are both on the order of 0.5-1.0 micron thick). Quantum well 104 is formed from undoped indium gallium nitride. As shown in FIG. 2, which illustrates a plane view of quantum well 104, indium clusters 201, localized regions of relatively high In content, are not distributed uniformly in quantum well 104. Individual indium clusters are generally formed with characteristic diameters of the order of 10 nm each.

Numerous studies have been reported to understand the detailed nature of the clustering and its effect on device performance. It is generally agreed that clustering severely affects device performance with the result that "green" LEDs are 3-5 times less efficient than "blue" or "red" LEDs (wherein efficiency can be measured by Lumens Out/Watts In). This effect is called the "green gap" in the LED industry. This severe reduction in internal quantum efficiency for green devices severely constrains white light LED brightness, color balance, and thermal packaging considerations for all applications in which three primary color LEDs (i.e. green, blue, and red) are used to generate "white light".

Currently, photoluminescence, electroluminescence, and transmission electron microscopy can be used to monitor post-epitaxial growth (i.e. a thin film of single crystal material formed over a single crystal substrate). Photoluminescence is typically performed with a tool that paints a spot size of roughly 5 microns diameter on the wafer. The use of a low NA (numerical aperture) lens and the wavelength of the light source yield this spot size. The result is that the average photo luminescence performance over a relatively large area of the wafer can be probed. Unfortunately, this area is roughly 2.5 to 3 orders of magnitude larger than the size of individual indium clusters 201. As a result, the fingerprints (i.e. any properties that can be measured and characterized) of indium clusters 201, which can indicate processed device performance, cannot be obtained using photoluminescence.

Electroluminescence probes even large areas of the wafer of course and therefore has even greater disadvantages. In contrast, transmission electron microscopy can be used to probe device morphology at high resolution. However, electron microscopy is very slow, expensive, and does not provide information on the manner in which morphology affects carrier mobility and recombination in quantum well 104 (such information being highly representative of LED performance).

Therefore, a need arises for an improved monitor for high-level indium InGaN quantum wells in LEDs.

SUMMARY OF THE INVENTION

A method of generating a photoluminescence map for an indium gallium nitride (InGaN) well can include presenting data on a pixel by pixel basis. In one embodiment, the data can be generated as a function of emission wavelength, line width of emission, polarization of emission, and intensity of emission. In another embodiment, the data can be generated as a function of excitation polarization and polarization angle orientation with respect to film crystalline axes of the InGaN well. In yet another embodiment, the data can be generated as a function of multiple wavelengths of light to generate the photoluminescence map.

The photoluminescence maps can be correlated to device internal quantum efficiency as measured in test devices, which have been characterized, processed, and tested for macroscopic emission properties. The resulting correlation maps can serve as line monitors of indium rich InGaN wafers used for green LEDs.

A system for performing the above-described method(s) can include a C-aperture, a transmitter, and spectrometer. The transmitter illuminates the C-aperture with wavelengths of light short enough to excite photocarriers in the InGaN well, wherein the light drives photoluminescence in the InGaN well. The spectrometer can analyze the photoluminescence in the InGaN well. In one embodiment, the system can further include a motion control device for moving the sample including the InGaN well.

DETAILED DESCRIPTION OF THE INVENTION

The indium rich InGaN that creates green LEDs can result in undesirable "clustering" of the indium. The degree of clustering is exceptionally sensitive to deposition conditions such as organometallic deposition gas flow rates, prior layer composition, as well as substrate temperature. The indium clusters are roughly 10-20 nm in spatial extent as noted earlier. Monitoring of the fingerprints of indium clustering and its effect on LED performance therefore requires a probe with exceptionally small point spread function or probe area. Because the probe wavelength is typically a wavelength that supports photoexcitation of carriers to just above the bandgap (and therefore green or blue photons), the point spread function of the probe source must be well below the wavelength of the source.

Figure 1:
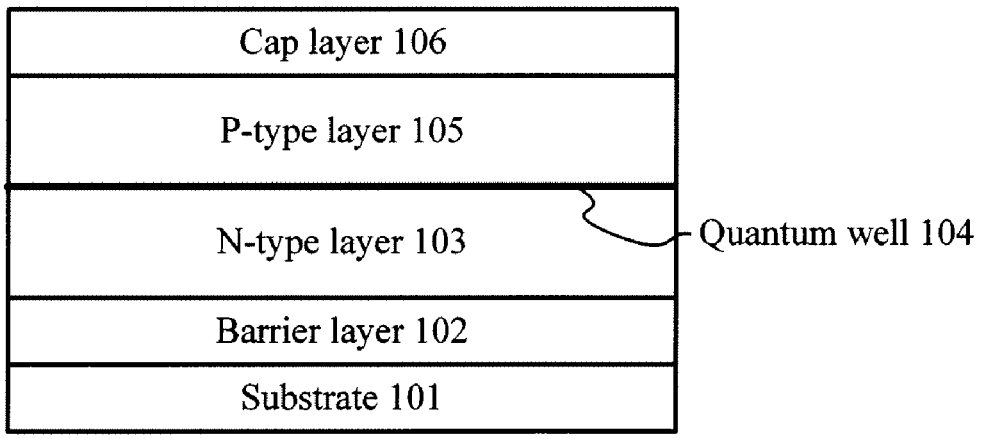
FIG. 1 illustrates an exemplary cross-section of an LED having an InGaN quantum well.
Figure 2:
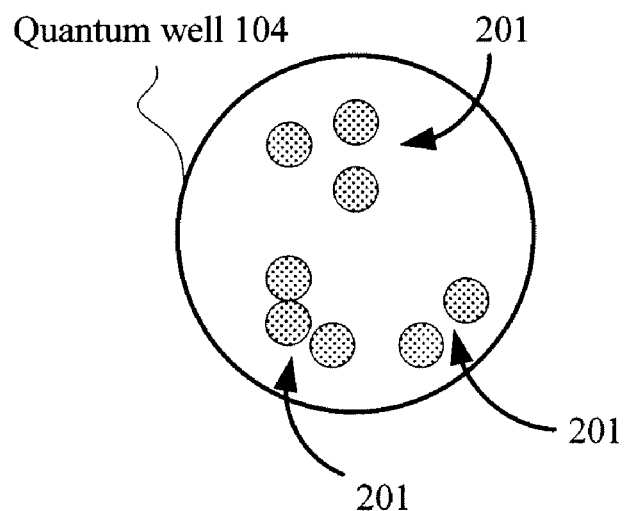
FIG. 2 illustrates a plane view of an exemplary InGaN quantum well.
Figure 3:
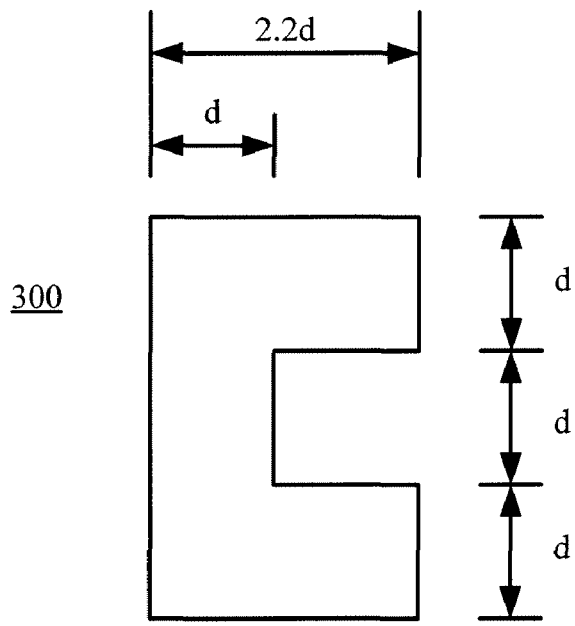
FIG. 3 illustrates an exemplary C-aperture that can be advantageously used for monitoring of indium clustering in an InGaN quantum well.

In accordance with one aspect of the invention, a sub-wavelength transmitting aperture can be used to probe the surface of a high-level indium InGaN quantum well. One such sub-wavelength transmitting aperture, a C-aperture, is described by Matteo, et. al. (J. A. Matteo, D. P. Fromm, Y Yuen, P. J. Schuck, W. E. Moerner, and L. Hesselink in App. Phys. Lett. Vol. 85(4), Jul. 26, 2004, pp. 648-650 and references therein). Notably, the C-aperture has wave-guiding properties that can overcome the exponential decay of film thickness (for a metal or dielectric) in transmitting wavelengths of light larger than the aperture. FIG. 3 illustrates an exemplary C-aperture 300. In one embodiment, C-aperture 300 can be ion-milled to form its very small notch, e.g. on the order of 10-20 nm.

Notably, C-aperture 300 can transmit light with efficiencies more than a million greater than unshaped apertures of similar size. For example, a common device now in use is an NSOM (near-field scanning optical microscope) in which tapered fiber lasers have a very sharp end, e.g. a radius of approximately 50 nm, which can deliver a sub-wavelength spot of light to a sample. However, the transmission of an NSOM is far less than a part in $10^3$ single pass. As a result, very weak beams of sub-wavelength light are delivered to the sample under observation. Therefore, images gathered using NSOM are taken very slowly due to the necessity to integrate signal for long periods to overcome detector noise. Compared to an NSOM, C-aperture 300 can advantageously provide dramatically more transmission, thereby providing both excellent resolution and imaging speed.

Figure 4:
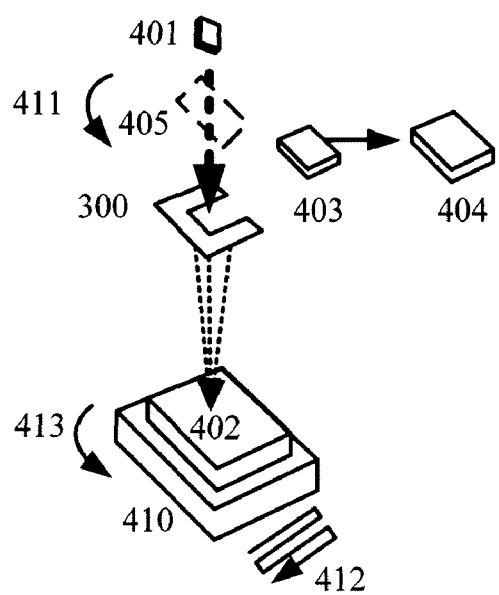
FIG. 4 illustrates an exemplary system for monitoring an InGaN quantum well.

FIG. 4 illustrates an exemplary system 400 including C-aperture 300. In system 400, C-aperture 300 can be placed into the face/path of a bright light transmitter 401. Transmitter 401 can be implemented using a laser diode, a diode-pumped solid state laser, a harmonically-converted solid state laser, a gas phase laser, a semiconductor diode laser, or another light transmitter in the range of 400-550 nm, of energy sufficient to excite luminescence in indium rich InGaN LEDs.

Advantageously, C-aperture 300 can direct the light/radiation from transmitter 401 (with wavelength above the bandgap of the InGaN quantum wells under examination) onto a sample 402 to interrogate the photoluminescence from the InGaN quantum wells with a spatial resolution less than or equal to 50 nm. In one embodiment, C-aperture 300 can be placed within 20 nm of sample 402 to allow monitoring. Using the beam splitter 405 and the spectrometer 403, this photoluminescence can be directed pixel by pixel into a detector 404.

Notably, C-aperture 300 transmits polarized radiation. Therefore, in one embodiment, the photoemission can be analyzed by spectrometer 403 as a function of wavelength and polarization with a resolution of 50 nm or better across selected areas of sample 402, typically on the order of 5×5 microns in extent. For example, in one embodiment, the beam splitter 405 may be a polarization element and can be placed between C-aperture 300, transmitter 401, and before spectrometer 403 and detector 404 to provide the desired polarization. Beam splitter 405 may be implemented using a Polaroid film or other optical devices. Beam splitter 405 may be rotated to provide different polarizations, as indicated by arrow 411

Furthermore, it may be desirable to extract these fingerprints (pixel by pixel data for emission wavelength, bandwidth, intensity, and polarization) by probing (photoexciting) the wafer with different polarizations of light aligned with different axes of sample 402 (i.e. polarization angle orientation with respect to film crystalline axes of the InGaN well). Note that, in one embodiment, data can be captured during serpentine swathes of sample 402, see e.g. arrow 412. These serpentine swathes can be performed using a motion control device 410 (e.g. a sample platform) which secures sample 402 to its top surface, thereby also moving sample 402 in a serpentine manner. During one of the serpentine swathes, sample 402 can first be rotated by a predetermined number of degrees (e.g. 90 degrees) using motion control device 410 as indicated by arrow 413, thereby providing data at a different orientation. Because InGaN is a piezoelectric material, the polarization signatures based on different orientations may be significant fingerprints of wafer quality. In one embodiment, different types of polarized light (e.g. planer, circular, elliptical) can be used for excitation and/or analysis.

Figure 5:
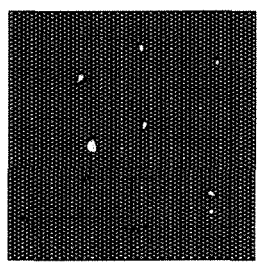
FIG. 5 illustrates an exemplary photoluminescence map (i.e. scanning images).

Advantageously, this C-aperture monitoring technique at the wafer film level can be performed at the very front end of the LED fabrication process. Moreover, this technique can quickly obtain data at 50 nm resolution to as low as 10 or 20 nm resolution. A hard vacuum is not required as in an e-beam tool. Data with respect to spatial resolution, intensity variation, emission wavelength variation, and polarization effects can be easily gathered using system 400. A map of these data, as generated by spectrometer 404, can then be correlated to device performance for process monitor and control on a wafer by wafer basis. FIG. 5 illustrates an exemplary photoluminescence map 500, i.e. a scanning image.

As explained above, the use of C-aperture technology can be advantageously used with an illumination source for interrogating at sub-wavelength (wavelengths short enough to photo excite carriers in InGaN quantum wells) spatial resolution (from 10 to 50 nm) the photoluminescence from indium rich InGaN quantum wells. In one embodiment, system 400 can be incorporated as a line monitor in a wafer fabrication process. Specifically, the photoluminescence maps generated using system 400 can be correlated to device internal quantum efficiency as measured in test devices (which have first been fully characterized, processed, and tested for macroscopic emission properties). The resulting correlation maps can serve as line monitors of indium rich InGaN wafers used for green LEDs.

This improved line monitor can characterize the details of indium clustering in green LEDs and map these details onto a predictable performance of wafers processed from each growth run. This improved line monitor will have high value as a disposition tool at the very front end of the process for LED growth. Moreover, this improved line monitor can assist the manufacturer in maintaining a much tighter process window for LED growth, thereby resulting in superior efficiency devices.

Although illustrative embodiments of the invention have been described in detail herein with reference to the accompanying figures, it is to be understood that the invention is not limited to those precise embodiments. They are not intended to be exhaustive or to limit the invention to the precise forms disclosed. As such, many modifications and variations will be apparent. For example, although a single C-aperture is described herein, other embodiments of the invention can use an array of C-apertures. Accordingly, it is intended that the scope of the invention be defined by the following Claims and their equivalents.

The invention claimed is:

1. A system comprising:
    a C-aperture;
    a transmitter for illuminating the C-aperture, wherein wavelengths of light emitted by the transmitter are short enough to excite photocarriers in an indium gallium nitride (InGaN) well, and wherein the light drives photoluminescence in the InGaN well; and
    a spectrometer for analyzing the photoluminescence in the InGaN well.

2. A system comprising:
    a C-aperture;
    a transmitter for illuminating the C-aperture, wherein wavelengths of light emitted by the transmitter are short enough to excite photocarriers in an indium gallium nitride (InGaN) well, and wherein the light drives photoluminescence in the InGaN well;
    a spectrometer for analyzing the photoluminescence in the InGaN well; and
    a motion control device for moving a sample including the InGaN well.

3. A method of generating a photoluminescence map for an indium gallium nitride (InGaN) well, the method comprising:
    presenting data on a pixel by pixel basis, the data being generated as a function of emission wavelength, line width of emission, polarization of emission, and intensity of emission.

4. The method of claim 3, wherein the data is also generated as a function of multiple wavelengths of light to generate the photoluminescence map.

5. The method of claim 3, wherein the photoluminescence maps are correlated to device internal quantum efficiency as measured in test devices, which have been characterized, processed, and tested for macroscopic emission properties.

6. The method of claim 5, further including using of resulting correlation maps to serve as line monitors of indium rich InGaN wafers used for green LEDs.

7. A method of generating photoluminescence maps for an indium gallium nitride (InGaN) well, the method comprising:
    presenting data on a pixel by pixel basis, the data being generated as a function of excitation polarization and polarization angle orientation with respect to film crystalline axes of the InGaN well.

8. The method of claim 7, wherein the data is also generated as a function of multiple wavelengths of light to generate the photoluminescence map.

9. The method of claim 7, wherein the photoluminescence maps are correlated to device internal quantum efficiency as measured in test devices, which have been characterized, processed, and tested for macroscopic emission properties.

10. The method of claim 9, further including using of resulting correlation maps to serve as line monitors of indium rich InGaN wafers used for green LEDs.

* * * * *